(12) United States Patent
Wong et al.

(10) Patent No.: US 10,489,901 B2
(45) Date of Patent: Nov. 26, 2019

(54) SYSTEM AND METHOD FOR INSPECTION OF WET OPHTHALMIC LENS

(71) Applicant: EMAGE VISION PTE. LTD., Singapore (SG)

(72) Inventors: Soon Wei Wong, Singapore (SG); Wen Sen Zhou, Singapore (SG); Sergey Smorgon, Singapore (SG); Kundapura Parameshwara Srinivas, Bangalore (IN)

(73) Assignee: EMAGE VISION PTE. LTD., Singapore (SG)

( * ) Notice: Subject to any disclaimer, the term of this patent is extended or adjusted under 35 U.S.C. 154(b) by 0 days.

(21) Appl. No.: 15/094,786

(22) Filed: Apr. 8, 2016

(65) Prior Publication Data
US 2017/0011507 A1    Jan. 12, 2017

Related U.S. Application Data

(63) Continuation of application No. PCT/SG2014/000473, filed on Oct. 8, 2014.

(30) Foreign Application Priority Data

Oct. 8, 2013    (SG) ............................. 201307605-4

(51) Int. Cl.
*G06T 7/00* (2017.01)
*G01N 21/896* (2006.01)
(Continued)

(52) U.S. Cl.
CPC ....... *G06T 7/0008* (2013.01); *G01M 11/0257* (2013.01); *G01M 11/0278* (2013.01);
(Continued)

(58) Field of Classification Search
CPC ......... G01M 11/0257; G01M 11/0278; G01M 11/0285; G01N 21/8851; G01N 21/896;
(Continued)

(56) References Cited

U.S. PATENT DOCUMENTS 4,727,325 A * 2/1988 Matsui .................. G01R 33/54
                                                         324/309
5,500,732 A    3/1996 Ebel et al.
(Continued)

FOREIGN PATENT DOCUMENTS

JP    2012073073 A    4/2012
WO    03073061 A2    9/2003

*Primary Examiner* — Edward Park
(74) *Attorney, Agent, or Firm* — King & Schickli, PLLC

(57) ABSTRACT

The present invention relates to an inspection system and more particularly to a system and method for inspection of wet ophthalmic lens, preferably in an automated lens manufacturing line. The inspection system provides for capturing multiple images of an ophthalmic lens using multiple cameras, each with a customized optical unit which may use wavelength filters, and the ophthalmic lens illuminated by multiple lighting modules each configured for a different wavelength, or a different polarization and triggered to strobe the illumination at the same instance or at different instances in the time domain. Suitable filters used in the optical module for each camera ensures appropriate images at different illuminating wavelength, especially when all the illuminations are strobed at the same time. Images captured and inspected by this configuration aids in improvement in method of inspection with enhanced degree of reliability and quality.

15 Claims, 8 Drawing Sheets

(51) Int. Cl.
  *G02C 7/04* (2006.01)
  *G01M 11/02* (2006.01)
  *G06T 7/60* (2017.01)
  *H04N 5/225* (2006.01)
  *H04N 5/247* (2006.01)
  *H04N 5/33* (2006.01)
  *H04N 5/372* (2011.01)
  *G01N 21/88* (2006.01)
  *G01N 21/958* (2006.01)
  *G02B 27/14* (2006.01)

(52) U.S. Cl.
  CPC ..... *G01M 11/0285* (2013.01); *G01N 21/8851* (2013.01); *G01N 21/896* (2013.01); *G01N 21/958* (2013.01); *G02C 7/04* (2013.01); *G06T 7/60* (2013.01); *H04N 5/2256* (2013.01); *H04N 5/247* (2013.01); *H04N 5/332* (2013.01); *H04N 5/372* (2013.01); *G01N 2021/8887* (2013.01); *G01N 2201/12* (2013.01); *G02B 27/141* (2013.01); *G06T 2207/10048* (2013.01); *G06T 2207/10152* (2013.01); *G06T 2207/30108* (2013.01)

(58) Field of Classification Search
  CPC ......... G01N 21/958; G01N 2021/8887; G01N 2201/12; G02C 7/04; G06T 7/0008; G06T 7/60; G06T 2207/10048; G06T 2207/10152; G06T 2207/30108; H04N 5/2256; H04N 5/247; H04N 5/332; H04N 5/372; G02B 27/141
  See application file for complete search history.

(56) References Cited

U.S. PATENT DOCUMENTS

| | | |
|---|---|---|
| 5,717,781 A | 2/1998 | Ebel et al. |
| 5,748,300 A | 5/1998 | Wilder et al. |
| 5,805,276 A | 9/1998 | Davis et al. |
| 6,765,661 B2 | 7/2004 | Biel et al. |
| 9,253,448 B1* | 2/2016 | Wang ............... H04N 7/18 |
| 2002/0163638 A1 | 11/2002 | Biel et al. |
| 2004/0008877 A1* | 1/2004 | Leppard ......... G01M 11/0214 |
| | | 382/141 |
| 2006/0029257 A1* | 2/2006 | Eguchi ............... G06T 7/0004 |
| | | 382/108 |
| 2006/0062104 A1* | 3/2006 | Kimura ............... G11B 7/1353 |
| | | 369/44.23 |
| 2008/0100621 A1* | 5/2008 | Aharon ............... G06T 7/60 |
| | | 345/424 |
| 2010/0183189 A1* | 7/2010 | Oh ............... G06F 17/30247 |
| | | 382/100 |
| 2010/0220905 A1* | 9/2010 | Katsuhara ............... G06T 7/68 |
| | | 382/128 |
| 2012/0327396 A1* | 12/2012 | Sites ............... G01M 11/0257 |
| | | 356/51 |
| 2015/0138540 A1* | 5/2015 | Newman ............... G01N 21/8803 |
| | | 356/124 |
| 2017/0011507 A1* | 1/2017 | Wong ............... G01N 21/896 |

* cited by examiner

| Defect | Illumination (650nm wavelength) WL3 | Illumination (550nm wavelength) WL2 | Illumination (450nm wavelength) WL1 |
|---|---|---|---|
| Holder location | X | | |
| No Lens | X | | |
| Lens location | X | | |
| Lens edge tracing | X | | |
| Flip lens | | X | |
| Bubble | X | X | X |
| Non circular | X | X | |
| Double lens edge | X | | |
| Tear | X | | |
| Gap | X | | X |
| Star burst | X | X | |
| Residual material | | X | X |
| Surface imperfection | X | X | |
| Visitint inclusion | X | X | X |

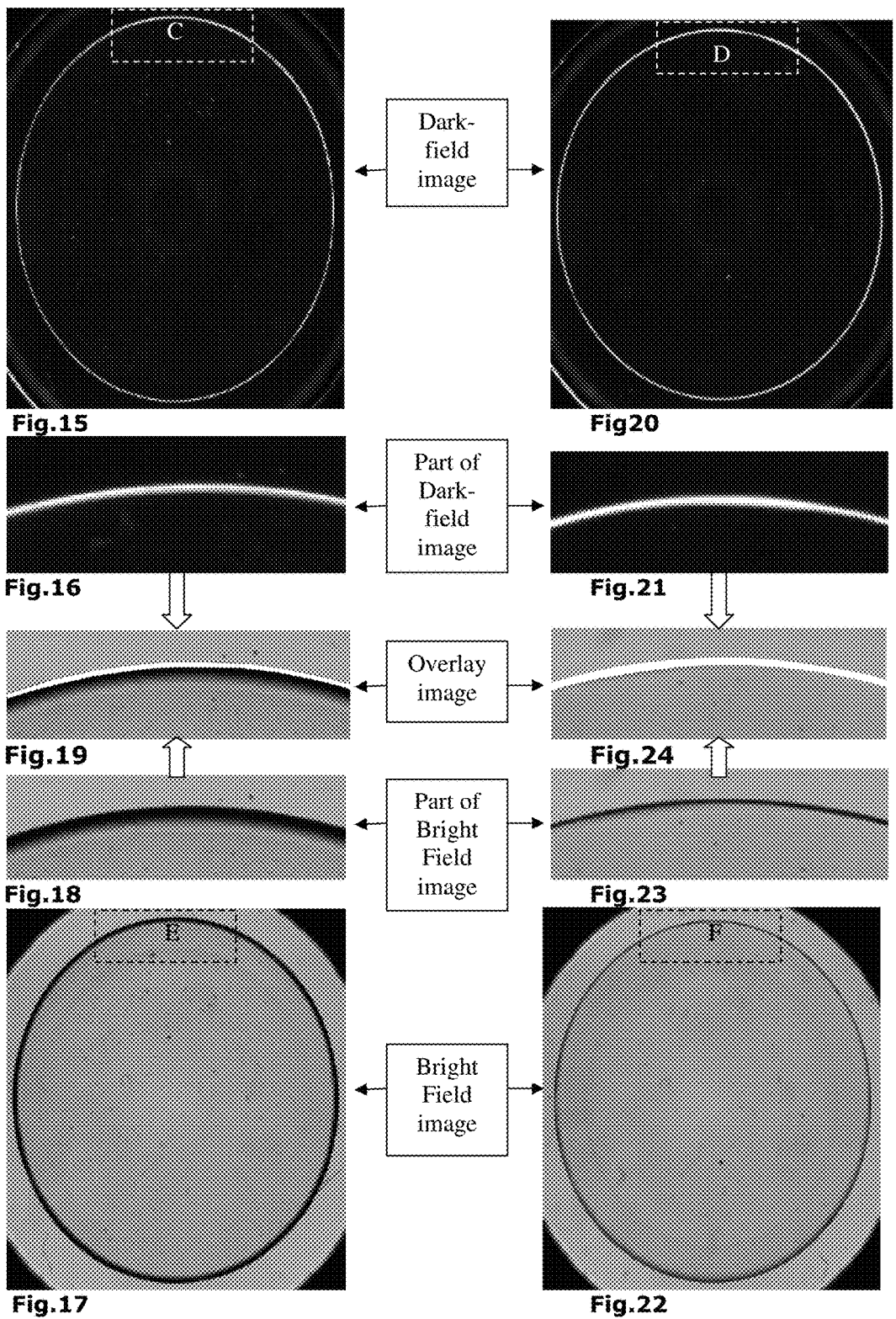

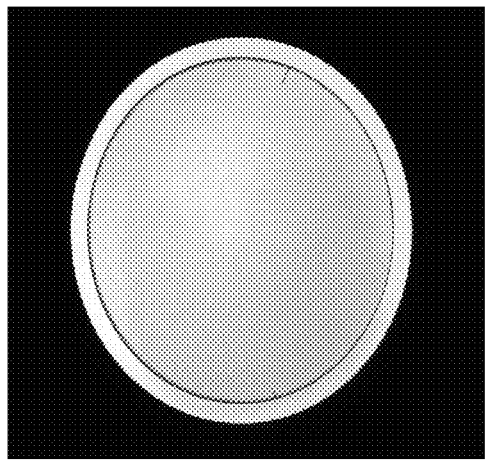
Fig.25
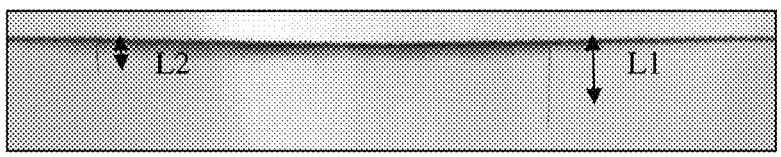
Fig.26
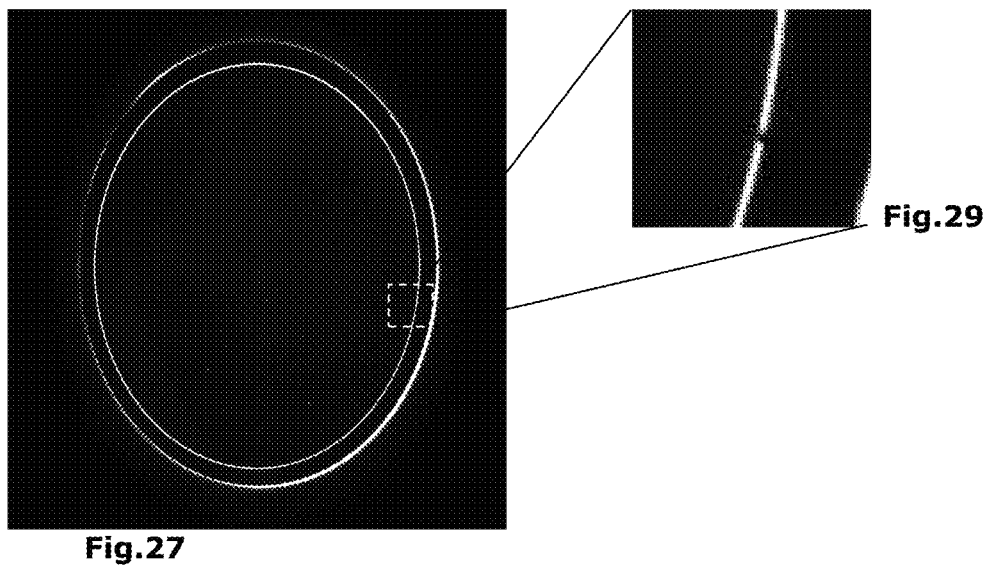
Fig.27
Fig.29
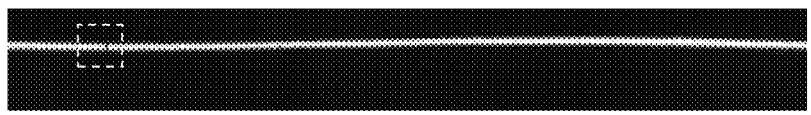
Fig.28

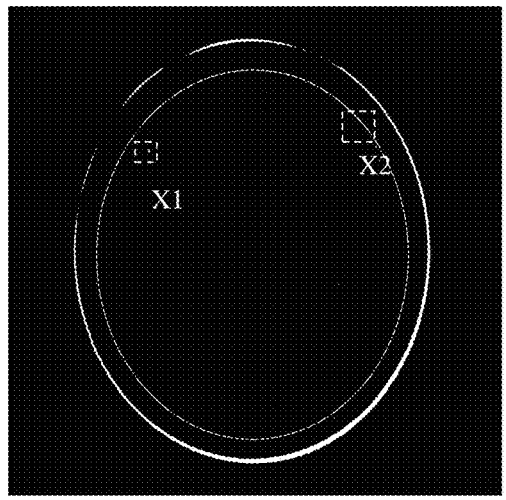
Fig.35
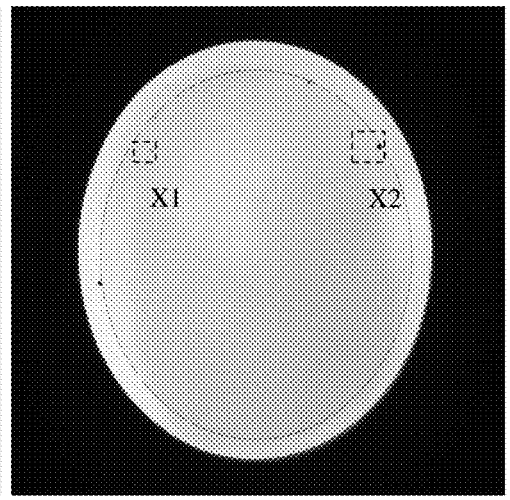
Fig.36
| Image No. | 1 | 2 | 3 | 4 | 5 |
|---|---|---|---|---|---|
| In Lens Bubble Defect X1 | | | | | |
| Air Bubble in Liquid X2 | | | | | |
Fig.37
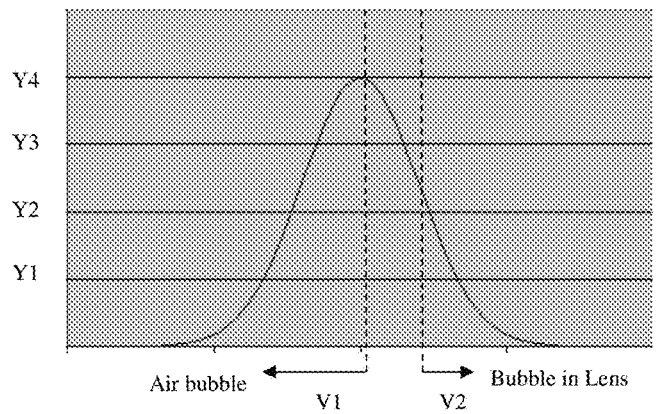
FIG 38

SYSTEM AND METHOD FOR INSPECTION OF WET OPHTHALMIC LENS

This application is a continuation of PCT/SG2014/000473, the disclosure of which is incorporated by reference, and which application qualifies as a U.S. patent application according to 35 USC 363 and contains a certified copy of Singapore patent application 201307605-4, which is also incorporated by reference.

TECHNICAL FIELD

The present invention relates to a system and method for inspection of wet ophthalmic lens, preferably in an automated lens manufacturing line. The inspection unit provides for a system of multiple cameras with high-resolution imaging sensors, which are configured to enable capturing of images using multiple channels of inspection, each channel consisting of at least one camera with a customized optical module and an illumination module for highlighting the ophthalmic lens to be inspected. The optical module for each channel may further constitute beam splitters and associated lens components to condition the light rays to achieve Dark-field and Bright field images depending upon the defects to be inspected. The present invention also provides for a method to inspect the said images captured by the said channel, which is configured for specific defect types, that greatly enhances the inspection quality.

BACKGROUND OF THE INVENTION

Ophthalmic lens is widely used and the high demand has created a need to produce very high quality lenses both standard and cosmetic lenses, in large quantities. It is a generally a known fact that lenses produced in an automated manufacturing line is more reliable than those manufactured by a manual system of production which suffers from unpredictable problems. It is also a widely accepted fact that inspection systems are an essential part of an automated manufacturing line to inspect the lenses and maintain a consistent and high quality inspection process to deliver premium quality product to customers. Regular tweaking of parameters and generating configuration files that contain inspection characteristics for various ophthalmic lens models enables flexible adaption of the inspection system for different types of lens. Ophthalmic lenses are intended for use in the human eye not just to correct the vision but also to enhance the cosmetic look of the eye by printing designs on the ophthalmic lens. Therefore great care must be taken to ensure that they are defect free. These ophthalmic lenses are produced in very high volumes in an automated manufacturing line. In order to ensure that each one of the lenses is manufactured as per strict quality control standards, it is essential that the lenses are inspected just before packaging, using automated inspection methods.

Before packaging, the ophthalmic lenses are placed in lens holders, which are transparent. Each holder holds one lens, which is generally immersed in a liquid solution. The wet lens inside the holder is inspected as the lens carrier moves along the conveyor in an automated manufacturing line. In order to increase the throughput of the manufacturing line, it is essential that the lenses are inspected as quickly as possible.

The holder used should preferably be made of clear glass with no coating on its bottom surface. Where the bottom surface of the holder is coated, it can result in images with uneven background.

The commonly used techniques for inspection of wet ophthalmic lenses are bright-field imaging, dark-field imaging and images captured using illumination in the Infra Red region. There are different types of illumination that use halogen lamps, xenon lamps, Lighting using LEDs. Etc. By using different illumination, many different types of defects are enhanced, which makes the images captured easy to detect very fine types of defects thus minimizing false rejects.

Prior Art U.S. Pat. No. 6,765,661 discloses the use of combining bright-field imaging and dark-field imaging in order to provide a good quality of inspection of defects. However, as is evident from later patents from the same inventor (Prior Art U.S. Pat. Nos. 7,663,742 and 7,855,782), the use of just bright field imaging in combination with dark-field imaging, is not enough for comprehensively inspect all types defects in anophthalmic lens.

Prior Art U.S. Pat. Nos. 7,855,782 and 7,663,742 disclose the use of combining phase contrast imaging along with either bright-field imaging or dark-field imaging in order to inspect all types of defects like accuracy of size, surface defects, tears, peripheral ruptures, inclusions such as bubbles and foreign bodies, as well as small defects at the edges of the ophthalmic lens.

In the prior arts discussed above inventions, monochromatic illumination light source is used along with beam splitters and other optics to split the light into secondary beams and one of the secondary beams is used for phase contrast imaging while the other is used for either bright-field imaging or dark-field imaging. By sequentially switching the light source for either bright-field imaging or dark-field imaging along with phase contrast imaging, complete inspection of the ophthalmic lens is achieved. This is time consuming and susceptible to Parasitic effect between illumination and external light. Furthermore, the use of holder with a flat bottom surface makes it difficult to consistently locate the edge of object to be inspected, as they can move around the holder. The lack in depth of focus also affects the sharpness of the image at the some areas of the ophthalmic lens, which impacts the edge detection ability and subsequent inspection of defects.

There is therefore a need for capturing multiple high-resolution images of the ophthalmic lens using multiple cameras for inspection, under different illumination wavelengths, different polarization, and to be able to trigger the illumination and camera shutters at the same instance or different instances as the user chooses, without sacrificing the image quality. This is the objective of the present invention.

SUMMARY OF THE PRESENT INVENTION

The present invention solves the problem by providing device in the form of a system architecture that renders itself to be configured for adding or removing inspection stations, without requiring too much space and eliminating the need to move the object from one inspection station to the next, thereby significantly reducing the inspection time and increasing the throughput of the manufacturing line.

In one aspect of the invention, a device is provided for capturing multiple images of an ophthalmic lens using multiple monochrome cameras, each with a customized optical module, which may or may not use filters for different wavelengths. The object to be inspected (ophthalmic lens) is illuminated by multiple illumination modules, each configured for a different wavelength or a different polarization and triggered to strobe the illumination at different times or at the same instance in the time domain.

In another aspect of the invention, the present invention provides a method for capturing multiple images of an ophthalmic lens using multiple monochrome cameras, each with a customized optical module which may or may not use different wavelength filters. The object to be inspected (ophthalmic lens) is illuminated by multiple illumination modules, each configured for a different wavelength or a different polarization and triggered to strobe the illumination at different times or at the same instance in the time domain In another aspect of the invention the system allows for simultaneous capturing of multiple Dark-field, Bright field images and high contrast images of the object or differently illuminated images of the object, from cameras of multiple inspection stations.

In another aspect of invention the system allows for separately capturing of multiple Dark-field, Bright field images, and high contrast images of the objector differently illuminated images of the object, from cameras of multiple inspection stations by selectively strobing the relevant illumination module at different instances in time.

In still another aspect of the invention, the present invention provides a device and method to capture and inspect multiple images of the object held in different forms of holders.

In still another aspect of invention, the present invention provides a device and method to capture and inspect multiple images of the object that are printed, tinted or simple transparent ophthalmic lenses.

Further details and advantages of the invention may be seen from the description and drawings that follow.

BRIEF DESCRIPTION OF THE DRAWINGS

It will be convenient to further describe the present invention with respect to the accompanying drawings that illustrate possible arrangements of the invention. Other arrangements of the invention are possible, and consequently the particularity of the accompanying drawings is not to be understood as superseding the generality of the preceding description of the invention.

FIG. 15 shows a dark-field image of normal lens.

FIG. 16 shows an enlarged image of the portion C of the dark-field image of FIG. 15.

FIG. 17 shows a bright-field image of the normal lens.

FIG. 18 shows an enlarged image of the portion E of the bright-field image of FIG. 17.

FIG. 19 is the resultant image after overlaying the images in FIG. 16 and FIG. 18.

FIG. 20 shows a dark-field image of a flipped lens.

FIG. 21 shows an enlarged image of the portion D of the dark-field image of FIG. 20.

FIG. 22 shows a bright-field image of the flipped lens.

FIG. 23 shows an enlarged image of the portion F of the bright-field image of FIG. 22.

FIG. 24 is the resultant image after overlaying the images in FIG. 21 and FIG. 23

FIG. 25 shows a Bright field image of a lens with tear defects.

FIG. 26 shows an unwrapped image of the edge area of the lens in FIG. 25

FIG. 27 shows an image of a lens with a gap defect

FIG. 28 shows an unwrapped image of the edge area of the lens in FIG. 27

FIG. 29 shows an enlarged image of the area where the gap defect is present.

FIG. 35 and FIG. 36 shows a Dark-field and Bright field image respectively, of a lens with bubble defects.

FIG. 37 shows a table that shows images at different threshold for area X1 and area X2 indicated in FIG. 35 and FIG. 36.

FIG. 38 shows a distribution curve of white to black pixel ratio in the X axis and the number of samples in the Y axis.

DETAILED DESCRIPTION OF THE INVENTION

According to the present invention, a preferred embodiment will be described with reference to the drawings mentioned.

The system of the present invention uses multiple cameras and optical modules to capture high-resolution images of the object that is illuminated using multiple illumination modules. The illumination modules are of varying wavelengths and may also be of different polarization. By using different wavelengths of illumination, the system when capturing images, is resistant to any parasitic effect between the illuminations, especially when they are strobed or triggered at the same time during image capture. The system also may use colour filters to eliminate all other wavelengths of light except for the filter wavelength. This system of interference prevention between captured images produces images that have defects that are enhanced. Quality images are thus obtained that improves quality of inspection significantly both in terms of accuracy and inspection speed.

Further, it has been found that in prior art systems, the depth of focus is a feature that is often compromised. The end result of images captured with systems using shallow depth of focus, as found in prior arts, is the lack of clarity of minute defects found in areas of the captured image that are fall out of the range of depth of focus. Depending upon the optical adjustments made for specific product types, the images captured of the ophthalmic lens appear sharp in certain regions and blurred in the other regions. Inaccurate measurement of defects leads to defective lenses entering the market. Furthermore, it has been found that having a bigger depth of focus in multiple camera systems poses a significant challenge.

The optical system of the present invention is designed to have a depth of focus that almost closely matches the curvature of the lens. This curved depth of focus range aids in capturing of sharp images of the entire profile of the lens. Locating the object with the holder is faster as the complete lens is well focused, irrespective of whether the holder has a curved recess or a flat recess for holding the lens. The resultant image when visualized by a user or analyzed by the computer program makes tears, bubbles, cuts and very low contrast defects easily visible and detectable.

Figures 1, 2, 3:
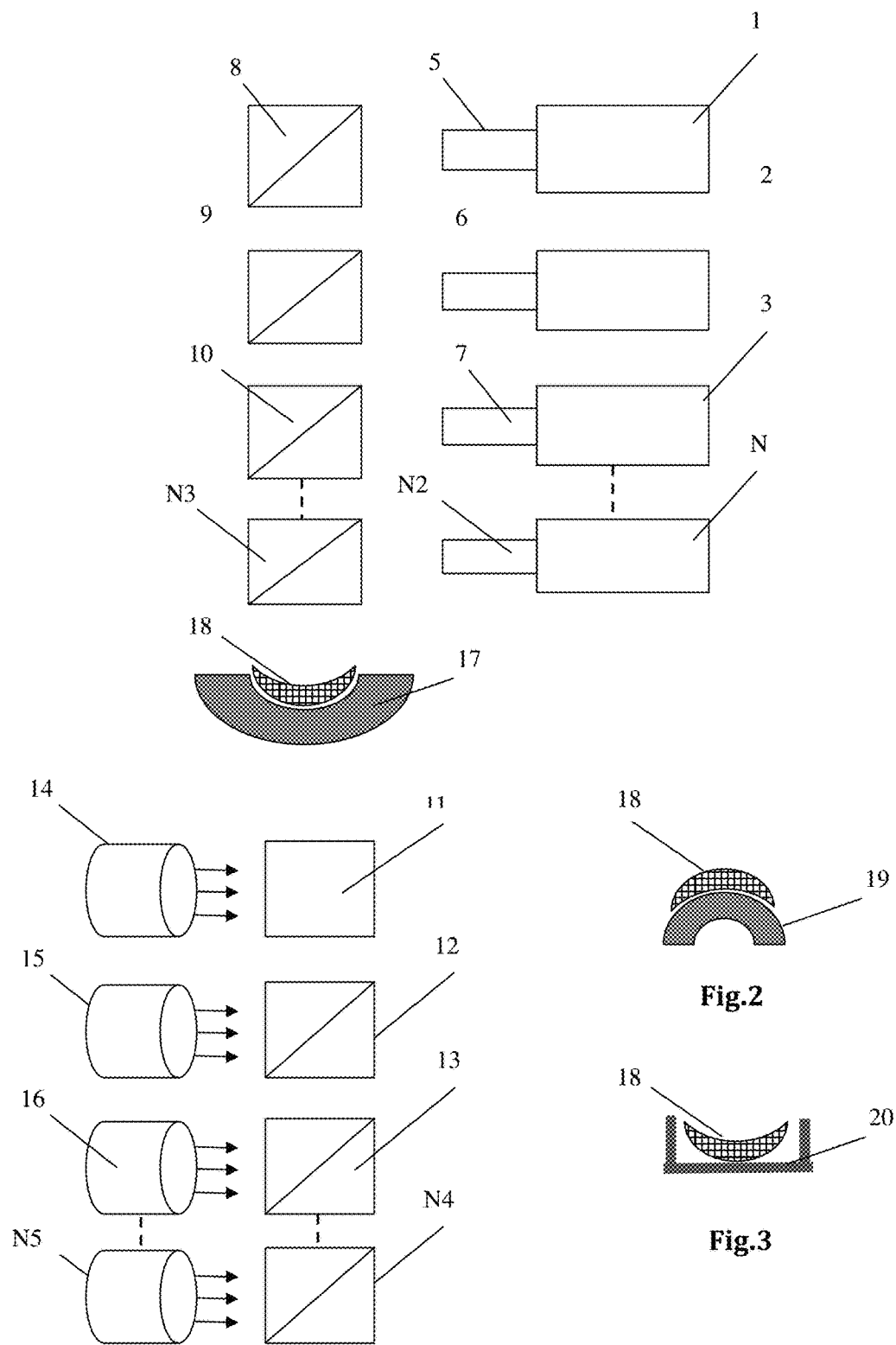
FIG. 1 shows an illustration of a multiple illumination modules and multiple cameras inspection system according to the present invention.
FIG. 2 shows a different lens holder for dry lens inspection, typically after the molding process.
FIG. 3 shows another holder with flat bottom surface usually containing a liquid (not shown)

As shown in FIG. 1, the system of the present invention uses "N" illumination modules and "N" cameras, a specially designed holder, beam splitters for directing the illumination from the illumination modules to the ophthalmic lens and then on to the respective cameras through specially designed optical modules for each camera, depending upon the type of feature to be inspected.

In a preferred embodiment of the invention, the illumination modules are strobed simultaneously to obtain multiple images simultaneously. Appropriate wavelength filters are used to eliminate any parasitic effect. The system uses monochrome cameras to achieve a higher resolution image. Furthermore, the different illumination modules maybe strobed at different time intervals and the multiple cameras are synchronized with the illumination strobe pulse to capture images. In some cases there is a need to implement time delays before capturing the image to suit the intensity requirements of the image. Delays are usually incorporated for camera shutter triggers when the time taken for the illumination to reach maximum intensity is slower. For example; when cameras are triggered at the same edge as the illumination, images tend to be blurred or faint depending upon the time the shutter is triggered. To enable a uniform intensity image, it is preferred to delay the camera shutter trigger by at least 50 microseconds, to enable the light intensity to reach its saturation point, after which the camera shutter is triggered. This technique results in a consistent image though the result of this method is the illumination strobe pulse is usually longer than the camera shutter pulse. The illumination control mechanism is not shown as it is outside the scope of this invention The optics of each of the "N2" channels is designed differently to cater for different illumination characteristics of the object. The system of illumination is configured using different wavelength light modules to produce Dark-field or Bright field images. The choice of illumination may have to be different for different type of defects. In such cases, the number of cameras and associated customized optics and illumination may have to be increased to cater to specific defect types which are better enhanced at specific wavelengths of light and magnification. Furthermore, with regards to the method of image capture, whether independent or simultaneous, may have to be evaluated to achieve the optimum image for the specific defect.

In an alternative embodiment, the monochrome cameras maybe replaced with colour cameras to obtain colour images at reduced resolution. The colour images captured render themselves for extraction in three different colours which can further be analyzed using appropriate algorithms to detect the defects in the extracted images.

It has to be noted that the present invention is directed towards an imaging system that uses multiple imaging devices and illuminations that enable a highly accurate and sharply focused image of the object (ophthalmic lens). Only then, is the said image suitable for efficiently detecting minute features or defects in a ophthalmic lens that includes but not limited to tears, cuts, bubbles, inclusions, ruptures, deformities, dimensional defect and foreign material contamination.

The system of the present invention enables capturing of multiple bright-field, dark-field and high contrast images. The ophthalmic lens to be inspected is held in a glass holder and suspended in a liquid. The holder is preferably made of clear glass without any coating at the bottom surface to prevent any inconsistency in the image that is captured. Non-uniform images are encountered when a glass holder with bottom coating is used. For this reason, it is recommended that a clear glass holder is used without any coating applied at the bottom surface. Irrespective of the design of the holder in which the ophthalmic lens is suspended in liquid, the optical system is so designed to have a depth of focus that closely matches the curvature of the ophthalmic lens. For example; if the holder of the lens has an internal radius of 14 mm and the lens has a radius of 8 mm, the optical system is designed to have a curved depth of focus of radius 11 mm, which ensures that the entire lens is in focus. The curved depth of focus enables locating the lens even if it has slighting shifted from the centre of the optical axis.

The holder in which the ophthalmic lens is positioned contains a liquid, such as, for example, water or saline or similar transparent solution. The holder is usually designed such that the ophthalmic lens therein is automatically centred at its bottom. However multiple types of holders are utilized to hold the lens, but due to the curved profile of the depth of focus designed into the optical module, the entire lens is in focus. The holder may be used as a standalone device or can be a part of bigger mechanism containing multiple holders.

In yet another embodiment of the invention, the holder holds the lens upside down as shown in FIG. 2. Lens positioned on such holders are common in molds that are used to manufacture the lens. In another embodiment of the invention a standard holder is used to position the lens under the inspection system. The holder has a flat bottom surface as shown in FIG. 3 and the lens is suspended in a liquid (not shown) inside the holder.

DETAILED DESCRIPTION OF DRAWINGS

Referring to FIG. 1, the inspection system consists of multiple Cameras 1, 2, 3 up to N numbers, which are mounted with optical modules 5, 6, 7 up to N2 numbers, respectively. The cameras are preferably monochrome cameras to capture high resolution images. Colour cameras may also be used in place of 5, 6, 7 and N sensors, but image resolution are lower compared with same resolution monochrome cameras.

A person skilled in the art will realize that both monochrome and Colour cameras may be utilized in the same system to suit the purpose of the inspection. The configuration of the optical modules 5, 6, 7 up to N2 varies depending upon the type of defects to be captured and the type of illumination to be utilized.

Figures 4, 5:
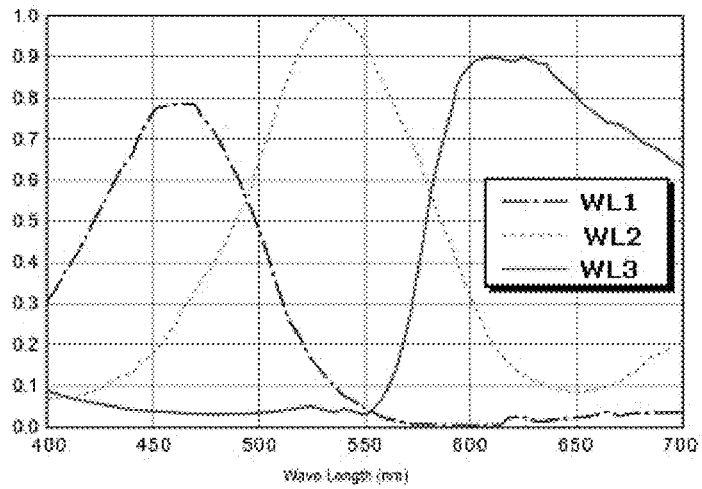
FIG. 4 shows the graph of spectral sensitivity of typical illumination devices of wavelength 1, 2 & 3 (WL1, WL2 and WL3) of the present invention.
FIG. 5 shows the table of typical defects commonly inspected in three different channels illuminated by three different wavelengths of illumination. (For example: Illumination modules emitting light at wavelengths of 650 nm, 550 nm & 450 nm)

The illumination modules 14, 15, 16 up to N5 are configured for different wavelengths of light WL1, WL2, WL3, etc to highlight different defects as indicated in the table of FIG. 5. More such illumination modules can be further incorporated with appropriate optical modules to enable detection of new type of defects. Fundamentally, the inspection system can be configured as required by adding new channels of inspection based on the requirements. Beam splitters 11, 12, 13 up to N4 deflect the light of a particular wavelength emerging from the illumination modules 14,15, 16 up to N5, to the ophthalmic lens 18, suspended in the holder 17. Beam splitters 8, 9, 10 up to N3 deflect the light transmitted through the lens 18 under inspection towards the customized optical modules 5, 6, 7 up to N2 respectively. Finally images are captured by cameras 1, 2, S up to N respectively after being conditioned by optical modules 5, 6, 7 up to N2. In effect N images are captured with different characteristics suited for inspection of different features in the ophthalmic lens.

Holder 17 as described earlier is made of monochromatic glass and does not have any coating on its surface to minimize image distortion.

In the preferred embodiment, the holder 17 containing the ophthalmic lens 18 immersed in a liquid (not shown) has a curved bottom surface to match the profile of the ophthalmic lens being inspected.

In another embodiment, as shown in FIG. 2, the holder could be of reverse flipped type 19 suitable for inspecting the lens in a dry state immediately after the lens molding process.

In yet another alternative embodiment, as shown in FIG. 3, the holder 20 could have a bottom surface that is of flat type, which is also suitable for wet lens inspection.

FIG. 4 shows the spectral sensitivity of the three illumination modules, which provide light at three different wavelengths. WL1 has a range 400 nm to 500 nm. Typically WL1 is configured for 430 nm. WL2 has a range 500 nm to 600 nm. Typically WL2 is configured for 550 nm. WL3 has a range 600 nm to 700 nm. Typically WL3 is configured for 650 nm.

The light emerging from illumination module 14 is of wavelength WL1, which has a range of 400 nm to 500 nm. Typically WL1 is configured for 450 nm. This light is comprised of scattered and reflected rays, which produces a dark-field image. Dark-field images highlight very low contrast defects and in certain cases defects with no contrast are also enhanced. Light from the illumination module 14 is deflected by beam splitter 11 on to the ophthalmic lens 18, which is immersed in liquid inside the holder 17. Beam Splitter 8 deflects the light emerging from the ophthalmic lens on to the optical filter 5 of the imaging system, which includes Camera 1. Column 4 of the table in FIG. 5 summarizes the defects covered by the first inspection channel, which uses light of wavelength WL1.

The light emerging from illumination module 15 is of wavelength WL2, which has a range of 500 nm to 600 nm. Typically WL2 is configured for 550 nm and it highlights defects to produce a high contrast image. Camera 2 is setup at a narrow aperture to capture images as a result of illumination provided by the light head 15 of wavelength WL2. At smaller apertures the illumination of the ophthalmic lens is at very narrow angles and this helps in capturing images with good contrast for most defects. Light from the illumination module 15 is deflected by beam splitter 12 on to the ophthalmic lens 18, which is immersed in liquid inside the holder 17. Beam Splitter 9 deflects the light emerging from the ophthalmic lens on to the optical filter 6 of the imaging system, which includes Camera 2. Column 3 of the table in FIG. 5 summarizes the defects covered by the second inspection channel, which uses light of wavelength WL2.

Illumination module 16 can be configured for a wavelength WL3, which has a range of 600 nm to 700 nm. Typically, WL3 is configured for 650 nm. The light of this wavelength highlights defects to produce a bright field image as the optical system directs the rays through the ophthalmic lens, producing either parallel, converging or diverging rays. Light from the illumination module 16 is deflected by beam splitter 13 on to the ophthalmic lens 18, which may be immersed in liquid inside the holder 17. Beam Splitter 10 deflects the light emerging from the ophthalmic lens on to the optical module 7 of the imaging system and on to the Camera 3. The light of wavelength WL3 has a wide beam of light and provides an image with uniform brightness across the full field of view. Bright-field imaging using this light produces a uniform image across a bigger field of view. Defects across the whole lens are easily measured, as illumination intensity is uniform. It should be noted that the image produced by the light of wavelength WL3 is not sensitive to the position of the ophthalmic lens in the liquid and a good image is captured of the ophthalmic lens irrespective of its positional shift. Column 2 of the table in FIG. 5 summarizes the defects that could be detected by the third inspection channel, which uses light of wavelength WL3.

A person skilled in the art will realize that an evaluation using different wavelengths of light maybe be performed and a table similar to the one shown in FIG. 5 can be arrived at. Based on the study, relevant illumination modules, appropriate optical modules, wavelength filters and relevant cameras can be selected to design the inspection channel. The architecture of the system enables easy addition or removal of inspection channels.

Examples of preferred illumination modules are light emitting diodes or short arc xenon flash lamps. Other illumination modules such as halogen lamps maybe used, in which case suitable filters may be required to achieve optimum image quality.

In another embodiment of the invention, an inspection channel maybe dedicated for capturing images with illumination modules operating in the Infrared spectrum.

In another embodiment of the invention, yet another inspection channel maybe configured to inspect features such as print quality.

In the preferred embodiment of the invention, the illumination modules are all strobed at the same instance of time and all the cameras simultaneously capture different images as per the corresponding light setting.

In an alternative embodiment of the invention, the illumination modules are strobed at different instances in the time domain and the corresponding cameras capture images as per the light setting.

In yet another embodiment of the present invention, the illumination modules used may be selectively turned OFF depending upon the type of defects to be inspected.

The illumination controller (not shown) is CPU controlled to change the intensity and pulse duration of the strobe. The CPU also controls the timing of the trigger pulse synchronization with respect to the camera shutter to get a consistent image quality. For the purpose of clarity the strobing mechanism and the art of image capture is not discussed as it is a well established technology of moving the images to computer memory. Images are then moved or copied to different memory locations for further image processing.

Figure 6:
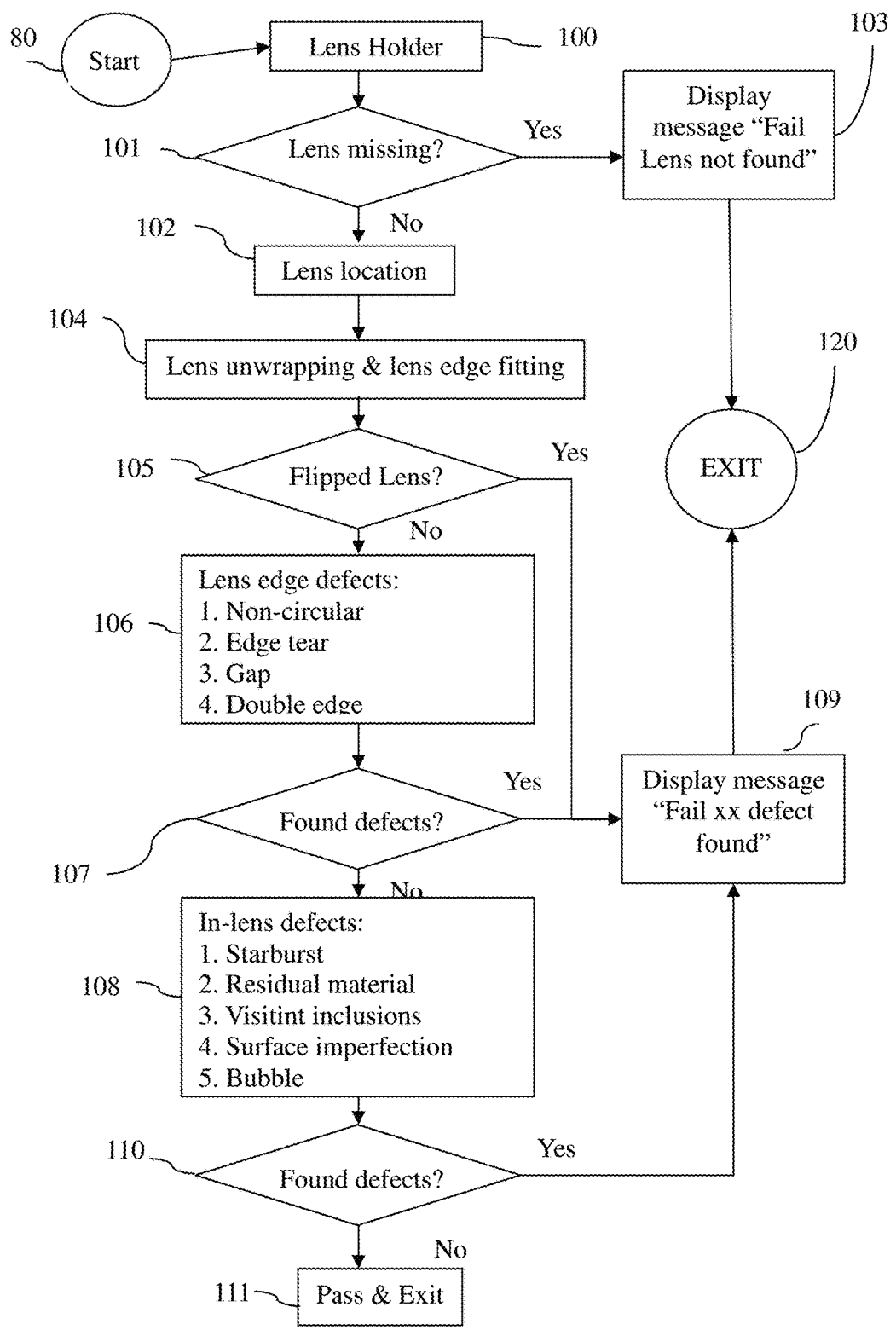
FIG. 6 shows the inspection flow chart for the system of the present invention.
Figure 7:
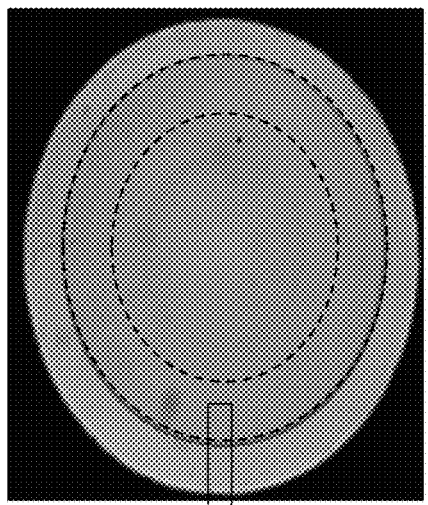
FIG. 7 shows the edge of a normal lens located in step 102 of the inspection flow chart.

Let us now refer to FIG. 6. It shows the flow chart for the process of inspection. Software algorithms begin the processing (at step 1) of the images in memory starting with sequence Step 100. In this step the lens holder is first detected followed by the lens edge in step 101. If the software can detect the lens inside the holder, the sequence of inspection moves to step 102. If the edge of the lens cannot be found, the sequence moves to step 103 to display an error message and exits at step 120. At step 102, the lens is located by edge finding algorithms after which a decision on presence or absence of a lens is made. At step 102 the lens edge is now located and the position is logged. In FIG. 7 shows the lens edge is indicated by the outer dashed circle.

Figure 8:
FIG. 8 shows the unwrapped image of a portion A of the lens image of step 102.
Figure 12:
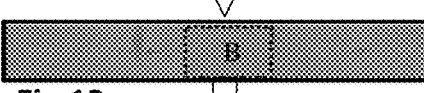
FIG. 12 shows the unwrapped image of a portion B of the lens image of step 102.

A first method relies on the lens structure and its characteristics. In this method, in step 104 a concentric area of lens as shown in FIG. 7 from the lens edge is selected and unwrapped for further processing. A second concentric circle is drawn with respect to the outer circle at a programmable distance from the outer circle with respect to the centre of the lens. The area within the two concentric circles is then unwrapped as shown in FIG. 8. Note that the unwrapped image is not drawn to scale. Many defects at the edges are detected using the unwrapped portion of the image.

Figure 9:
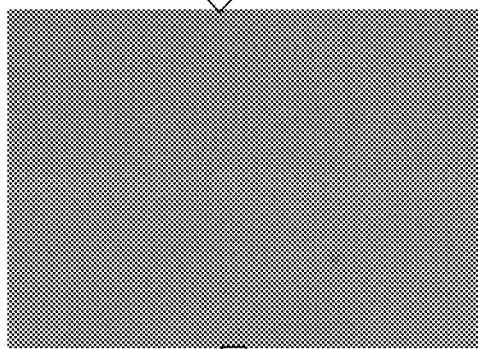
FIG. 9 shows the image of a small portion extracted from the unwrapped image in FIG. 8.
Figure 13:
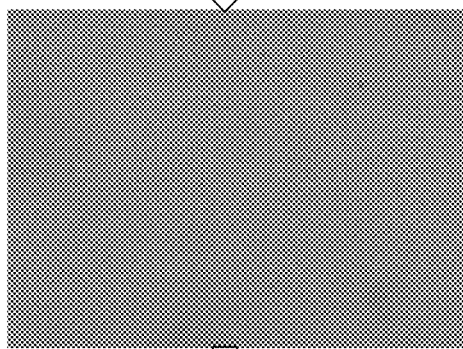
FIG. 13 shows the image of a small portion extracted from the unwrapped image in FIG. 12.
Figure 10:
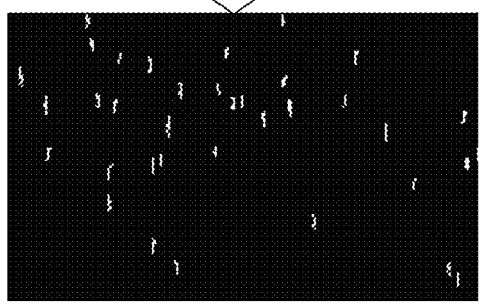
FIG. 10 shows FIG. 9 image after binarization.

In the next step 105, inspection for a flipped lens is done. A small area A is selected as programmed by the user. For E.g.: Area A is extracted (FIG. 9) and maybe processed by using binarization technique. The resulting image shown in FIG. 10 shows an image with white vertical lines.

Figure 11:
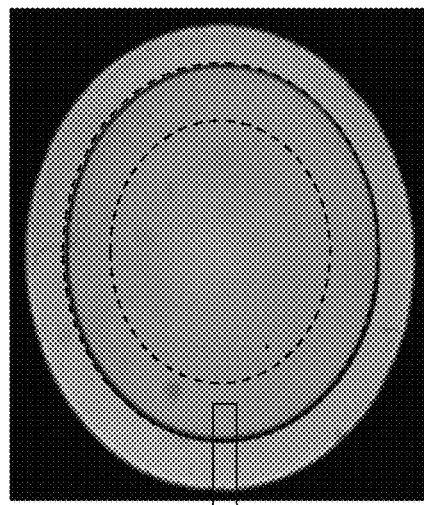
FIG. 11 shows the edge of a flipped lens located in step 102 of the inspection flow chart.
Figure 14:
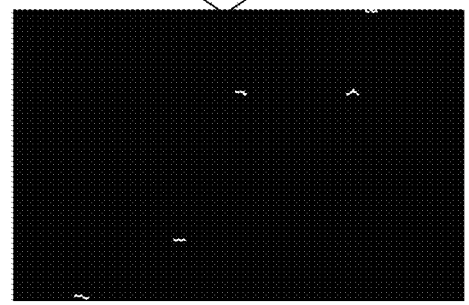
FIG. 14 shows FIG. 13 image after binarization.

Another image as shown in FIG. 11 is also processed the same way as FIG. 7 by choosing another area such as B and binarised. The resulting binarised image in FIG. 14 shows horizontal lines.

The lens structure is such that due to its poor Signal-to-Noise ratio characteristics, normal lens has vertical lines in its binarised image and a flipped lens shows Horizontal lines in the binarised image. Based on the orientation of the lines in the binarised image, a decision is made at step 105. If the lens is determined as flipped, the sequence moves to step 109. If the lens is found to be normal or not flipped the sequence moves to step 106 where the next set of defects are detected.

A second method is described herein to detect a flipped lens. FIG. 15 shows a dark-field image of normal lens. FIG. 16 shows an enlarged image of the portion C of the lens in FIG. 15. The edge of the lens shows a white curved thick line. FIG. 17 shows a bright field image of the same lens. FIG. 18 shows an enlarged image of the portion E of the bright field image of FIG. 17. As evident, the dark edge of the bright field image is thicker than the white edge of the dark-field image in FIG. 16. When image in FIG. 18 is overlayed with image in FIG. 16, the resulting image in FIG. 19 shows a thin white edge followed by dark edge.

FIG. 20 is a dark-field image of a flipped lens and FIG. 21 is an enlarged image of a portion D of the lens in FIG. 20. The edge shows a white edge quite similar to the image in FIG. 16 of a normal lens. Further, FIG. 22 is a bright field image of a flipped lens and FIG. 23 is an enlarged image of a portion F of the lens in FIG. 22. The dark edge of the bright field image in FIG. 23 is thinner when compared with the dark edge in the bright field image of a normal lens as in FIG. 18. When image in FIG. 23 and image in FIG. 21 is overlayed, the resulting image in FIG. 24 shows a white edge followed by a faint dark line. The phenomenon of the dark edge not expanding over the white edge in case of a flipped lens is a key feature that is inspected, to determine the difference between a normal lens and a flipped lens. After evaluating many different samples of the lens, it has been found that a threshold percentage maybe arrived at using the White edge width and Dark edge width. This parameter may be used to accurately detect a normal and flipped lens.

If the lens is inspected to be normal, the inspection moves to step 106 where all defects related to the lens edge is inspected.

FIG. 25 shows an image of an ophthalmic lens which has tear defect. In this image the process of locating the lens, the lens edge and unwrapping is similar to the steps explained in 102 and 104 of the flow chart shown in FIG. 6. On unwrapping the image the software checks the height of the tear L1 and L2 (FIG. 26) with respect to the edge of the lens. Based on the user defined defect criteria the program decides if the lens tear is a defect or not.

FIG. 27 shows another image of an ophthalmic lens with a gap defect. In this image the same process of extracting the edge and unwrapping the concentric area, is executed. An unwrapped image is shown in FIG. 28. An enlarged area of Gap defect is shown in FIG. 29 and the position of the defect in the unwrapped image is indicated in FIG. 28. Here again, based on the user defined defect criteria the program decides if the lens is defective or not.

Figure 30:
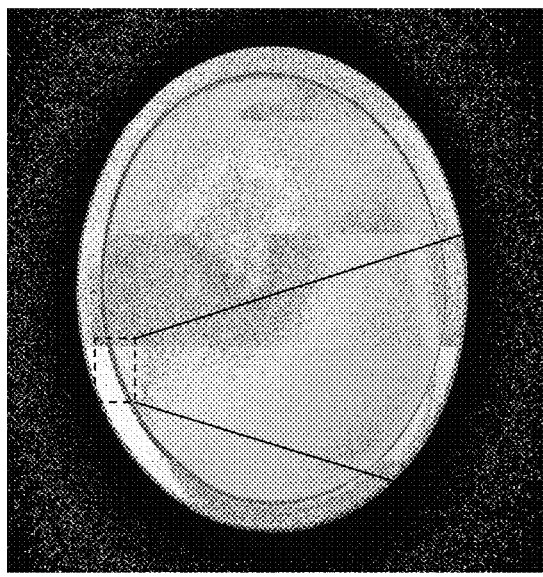
FIG. 30 shows an image of a lens with double edge defect
Figure 32:
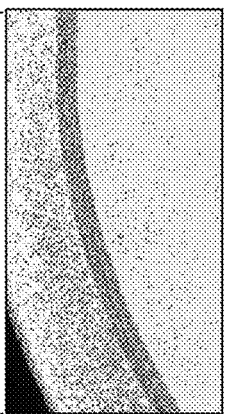
FIG. 32 shows an enlarged image of the area where the double edge defect is present.
Figure 31:
FIG. 31 show an unwrapped image of the edge area of the lens in FIG. 30

FIG. 30 shows an image of a double edge ophthalmic lens. The enlarged image FIG. 32 and the unwrapped image in FIG. 31 show a white line between two black lines indicating a double edge lens. This phenomenon of a white line between the black lines is determined as a double edge defect. Further processing of comparing the dimensions of this defect compared with the user set defective criteria is done decide whether the lens is defective or not.

Figure 33:
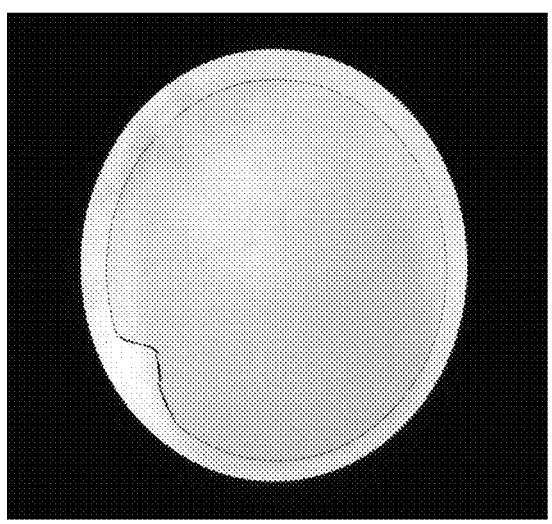
FIG. 33 shows an image of a lens with a non-circular defect
Figure 34:
FIG. 34 shows an unwrapped image of the edge area of the lens in FIG. 33

FIGS. 33 and 34 show an image of a non-circular lens. The process of locating the edge and unwrapping the lens area is done as per step 102 and 104. The distance from the line edge to the non-circular area is measured and then compared with the user defined rejection criteria to decide is the lens is a reject or not.

While a few processing methods are explained, a person skilled in the art will realize, the software can be configured to measure other types of inclusions at the edge. Once the edge defect inspection is completed, the sequence moves to step 107 where the program checks if defects were found in Step 106. If yes, the sequence jumps to 109 and further to step 120.

If no defect was found in step 107, the sequence moves to step 108. The process to detect defects within the lens begins here. The method of inspection described below relates to bubbles found within the lens and air bubbles typically found on the surface of the lens. To reduce overkill of rejects due to air bubbles, a novel method is explained below. One skilled in the art will realize that the same set of algorithms with minor changes to the process steps can be used to detect most in-lens defects with no change in the fundamental algorithm.

FIG. 35 and FIG. 36 shows a dark-field image of a lens and FIG. 36 shows a bright field image of the same lens in FIG. 35. After analysis two spots have been selected X1 and X2. The two areas X1 and X2 have been binarized at different thresholds and a total of four images have been logged in the table shown in FIG. 37. Image 2 of X1 shows a bigger white area than the white area of X2 in image 2.

However image 1 of X1 shows a smaller darker area compared to image 1 of X2. The same applies to images 3 and 4. After several experiments, it has been found that if the percentage ratio of white area to black area is greater than 35%, a bubble inside the lens exists. However for a ratio percentage of white area to black area less than 25%, an air bubble is present in that position. For any percentage value falling between 25% and 35%, further processing maybe required which may include, but not limited to, overlay method. The overlay method involves the method of overlaying two images, in this case image in column 1 and 2. In the case of defect X1 where a bubble is within the lens, the resulting image shows the white area almost merging with the black area. However in the case of X2 where the bubble is actually an air bubble, the resulting overlay image shown in Column 5 for X2, the white area is surrounded by a black ring. The overlay method is an enhanced method to detect very fine in-lens bubbles which may exist in the lens.

Further processing is done to determine other defects in step 108, which will not be discussed in detail. In step 110, the program checks if any defects were found in step 108. If yes, the sequence moves to step 109 and further to step 120 to exit the program. If no defects were found in Step 110, the program sequence moves to step 111, by the passing the inspected ophthalmic lens before exiting the program.

The present invention is preferably used in an automated manufacturing line where the specimen (ophthalmic lens) is transported along a predetermined path and positioned under the inspection station for inspection. Preferably the ophthalmic lens is moving through the inspection system. However the ophthalmic lens may also be inspected in a stationary position, if the inspection process requires it.

In the foregoing description the invention has been described with reference to specific embodiments thereof. It will, however, be evident that various modifications and changes may be made thereto by a skilled person in the art, without deviating from the broader spirit and scope of the invention. For eg: One such embodiment may be in the form of using a single colour or monochrome camera in conjunction with multiple illumination modules, configured to capture multiple images of the same object at different time domains. The specification and drawings are, accordingly, to be regarded as illustrative rather than a restrictive sense.

The method described above is suitable to inspect all kinds of ophthalmic lenses, preferably soft conventional hydrogel contact lens, comprising poly-HEMA homo or copolymer, a PVA homo or copolymer, or a cross linked polyethylene glycol or polysiloxane hydrogel.

The invention claimed is:

1. Process for inspecting an ophthalmic lens, comprising:
 placing the lens on a curved surface of a holder;
 providing a plurality of illumination modules for illumination the ophthalmic lens, each of the plurality of illumination modules is arranged to be selectively strobed;
 acquiring multiple images by a plurality of optical detectors or imaging devices and subsequently processed and analyzed in the image analyzing equipment by image processing algorithms for detecting defects in the ophthalmic lens, drawing two or more concentric circles on the captured images, and converting an area of interest encompassed by the two or more concentric circles to form a two dimensional image; and
 analyzing a flipped lens, the analyzing steps including:
 defining an area in the image by a small box;
 binarizing the area in the box by defining a said light intensity threshold value to separate the Dark and White pixels;
 identifying the white pixel groups in the area; and
 evaluating the geometric characteristic of at least one white pixel group;
 wherein each of the plurality of illumination modules is arranged to emit different wavelengths of illumination; and
 wherein the plurality of optical detectors or imaging devices are suitably coupled with a plurality of beam splitters and a plurality of optical filters, the beam splitters and optical filters are arranged to guide the different wavelengths of illumination to the respective optical detectors or imaging devices.

2. Process according to claim 1, wherein said geometric characteristic includes the height of at least one white pixel group.

3. Process according to claim 1, wherein said geometric characteristic includes the width of at least one white pixel group.

4. Process according to claim 1, wherein said geometric characteristic includes the aspect ratio of at least one white pixel group.

5. Process according to claim 1, wherein said geometric characteristic includes the step of counting the number of white pixel groups in the horizontal orientation and a subsequent step of rejecting the lens, if it exceeds a predetermined count.

6. Process according to claim 1, further includes the steps for analyzing gap defects in ophthalmic lens, the steps including:
 a) identifying the edge of the lens in the unwrapped image in FIG. 27, resulting in image shown in FIG. 28;
 b) locating a gap in the edge profile in the unwrapped image of the lens in FIG. 28;
 c) measuring the length of gap identified in step b.

7. Process according to claim 6, wherein said geometric characteristic includes the step of comparing the gap distance with the user set values and a subsequent step of rejecting the lens if the gap value exceeds the user set limits.

8. Process according to claim 1, further includes the steps for analyzing double edge defects in ophthalmic lens, the steps including:
 a) identifying the edge of the lens in the unwrapped image of the image in FIG. 30 resulting in image shown in FIG. 31;
 b) locating a white pixel blob in between two black edges in the edge profile of the unwrapped image of the lens edge in FIG. 28;
 c) measuring the geometric characteristic of the White pixel blob.

9. Process according to claim 8, wherein said geometric characteristic includes the step of calculating the area of the blob and the subsequent step of rejecting the lens if the blob area value exceeds the user set limits for double edge defective lens.

10. Process according to claim 1, further includes the steps for analyzing non-circular defects in ophthalmic lens, the steps including:
 a) Identifying the edge of the lens in the unwrapped image of the image in FIG. 33 resulting in image shown in FIG. 34;
 b) Measuring the geometric characteristic as in the vertical height at different points from the imaginary line of a normal edge lens line with that of the actual line identified in step a.

11. Process according to claim 10, wherein said geometric characteristic includes the step of comparing the various height values measured at different points and the subsequent step of rejecting the lens if the values of the heights measured exceeds the user set limits for a non-circular defective lens.

12. Process for inspecting an ophthalmic lens, comprising:
    placing the lens on a curved surface of a holder;
    providing a plurality of illumination modules for illuminating the ophthalmic lens, each of the plurality of illumination modules is arranged to be selectively strobed;
    acquiring multiple images by a plurality of optical detectors or imaging devices and subsequently processed and analyzed in the image analyzing equipment by image processing algorithms for detecting defects in the ophthalmic lens;
    drawing two or more concentric circles on the captured images, and converting an area of interest encompassed by the two or more concentric circles to form a two dimensional image; and
    analyzing a tear defects in ophthalmic lens, the steps including:
    identifying the edge of the lens in the unwrapped image of an area around the edge in FIG. 25, resulting in image shown in FIG. 26;
    measuring the length of tear L1 and L2 in the image shown in FIG. 26;
    evaluating the geometric characteristic of L1 and L2;
    wherein each of the plurality of illumination modules is arranged to emit different wavelengths of illumination; and wherein the plurality of optical detectors or imaging devices are suitably coupled with a plurality of beam splitters and a plurality of optical filters, the beam splitters and optical filters are arranged to guide the different wavelengths of illumination to the respective optical detectors or imaging devices.

13. Process according to claim 12, wherein said geometric characteristic includes the step of measuring the height of the tear L1 and L2 and a subsequent step of rejecting the lens if the height value exceeds the user set limits.

14. Process according to claim 12, wherein said geometric characteristic includes the step of measuring the width of the tear L1 and L2 and a subsequent step of rejecting the lens if the width value exceeds the user set limits.

15. Process for inspecting an ophthalmic lens, whereby multiple images are acquired by a plurality of optical detectors or imaging devices and subsequently processed and analyzed in the image analyzing equipment by image processing algorithms to detect defects in the ophthalmic lens, the process including the steps of:
    extracting an edge from the captured images;
    drawing a concentric circle from the edge of the lens pre-programmed offset;
    unwrapping the area within the two concentric circles to form a two dimensional image;
    analyzing a flipped lens, wherein the step of analyzing the flipped lens includes:
    a) defining an area in the image by a small box;
    b) binarizing the area in the box by defining a light intensity threshold value to separate dark and white pixels;
    c) identifying white pixel groups in the area;
    d) evaluating a geometric characteristic of at least one white pixel group.

* * * * *